US012558241B2

(12) United States Patent
Liu et al.

(10) Patent No.: US 12,558,241 B2
(45) Date of Patent: Feb. 24, 2026

(54) DEGRADABLE DRUG-LOADED STENT AND MANUFACTURING METHOD THEREFOR

(71) Applicant: SHANGHAI MICROPORT MEDICAL (GROUP) CO., LTD., Shanghai (CN)

(72) Inventors: Wei Liu, Shanghai (CN); Xueqin Wang, Shanghai (CN); Yaqin Gao, Shanghai (CN); Fan Qi, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 1062 days.

(21) Appl. No.: 17/595,131

(22) PCT Filed: May 9, 2020

(86) PCT No.: PCT/CN2020/089349
§ 371 (c)(1),
(2) Date: Nov. 9, 2021

(87) PCT Pub. No.: WO2020/228629
PCT Pub. Date: Nov. 19, 2020

(65) Prior Publication Data
US 2022/0079786 A1 Mar. 17, 2022

(30) Foreign Application Priority Data

May 10, 2019 (CN) .......................... 201910389694.5

(51) Int. Cl.
*A61F 2/915* (2013.01)
*A61F 2/82* (2013.01)
(Continued)

(52) U.S. Cl.
CPC .............. *A61F 2/915* (2013.01); *A61L 31/16* (2013.01); *B23K 26/38* (2013.01); *A61F 2/82* (2013.01);
(Continued)

(58) Field of Classification Search
CPC .... A61F 2/915; A61F 2/90; A61F 2/82; A61F 2/04; A61F 2/06; A61F 2002/91558; A61F 2210/0004; A61F 2250/0067; A61L 31/16
See application file for complete search history.

(56) References Cited

U.S. PATENT DOCUMENTS

| | | | |
|---|---|---|---|
| 2004/0117005 A1 | 6/2004 | Nagarada Gadde et al. |
| 2004/0172124 A1 | 9/2004 | Vallana et al. |
| 2008/0317827 A1 | 12/2008 | Wright et al. |

FOREIGN PATENT DOCUMENTS

| | | |
|---|---|---|
| CN | 1605366 | 4/2005 |
| CN | 201019862 Y | 2/2008 |

(Continued)

OTHER PUBLICATIONS

Notice of Reasons for Refusal issued for Japanese Patent Application No. 2022-514032, Dispatch Date: Jan. 30, 2023, 11 pages including English machine translation.

(Continued)

*Primary Examiner* — Dinah Baria
(74) *Attorney, Agent, or Firm* — HSML P.C.

(57) ABSTRACT

A degradable drug-loaded stent and a manufacturing method therefor. The degradable drug-loaded stent comprises a stent body, an outer surface of the stent body being provided with a drug-loaded groove, the stent body having a contracted state and an expanded state, the stent body being capable of switching from the contracted state to the expanded state via radial expansion, the stent body being a mesh columnar (Continued)

structure when in the expanded state, the depth of the drug-loaded groove being 10%-60% of the wall thickness of the mesh columnar structure.

11 Claims, 9 Drawing Sheets

(51) Int. Cl.
  *A61F 2/90*       (2013.01)
  *A61L 31/16*      (2006.01)
  *B23K 26/38*      (2014.01)
(52) U.S. Cl.
  CPC ....... *A61F 2/90* (2013.01); *A61F 2002/91558*
      (2013.01); *A61F 2210/0004* (2013.01); *A61F*
          *2240/001* (2013.01); *A61F 2250/0067*
                                        (2013.01)

(56)                References Cited

FOREIGN PATENT DOCUMENTS

| | | | | | |
|---|---|---|---|---|---|
| CN | 101879102 | | 11/2010 | | |
| CN | 102379762 | | 3/2012 | | |
| CN | 103582466 | | 2/2014 | | |
| CN | 203677324 | U | 7/2014 | | |
| CN | 104053457 | | 9/2014 | | |
| CN | 106137483 | | 11/2016 | | |
| CN | 107049571 | | 8/2017 | | |
| CN | 107088110 | | 8/2017 | | |
| CN | 206482699 | U | 9/2017 | | |
| CN | 108938158 | | 12/2018 | | |
| EP | 2740445 | B1 | * 12/2015 | .............. | A61F 2/91 |
| JP | H05200048 | A | 8/1993 | | |
| JP | 2012507375 | A | 3/2012 | | |
| JP | 2013500088 | A | 1/2013 | | |
| JP | 2013544573 | A | 12/2013 | | |
| JP | 2018078990 | A | 5/2018 | | |
| KR | 101392770 | B1 | 5/2014 | | |
| WO | 2010127584 | A1 | 11/2010 | | |

OTHER PUBLICATIONS

Decision to Grant a Patent issued for Japanese Patent Application No. 2022-514032, Dispatch Date: Jul. 18, 2023, 4 pages including English translation.
Hearing Notice issued for Indian Patent Application No. 202147055886, Date of Dispatch: Jul. 29, 2024, 2 pages.
International Search Report issued for International Patent Application No. PCT/CN2020/089349, Date of mailing: Sep. 23, 2020, 10 pages including English translation.

* cited by examiner

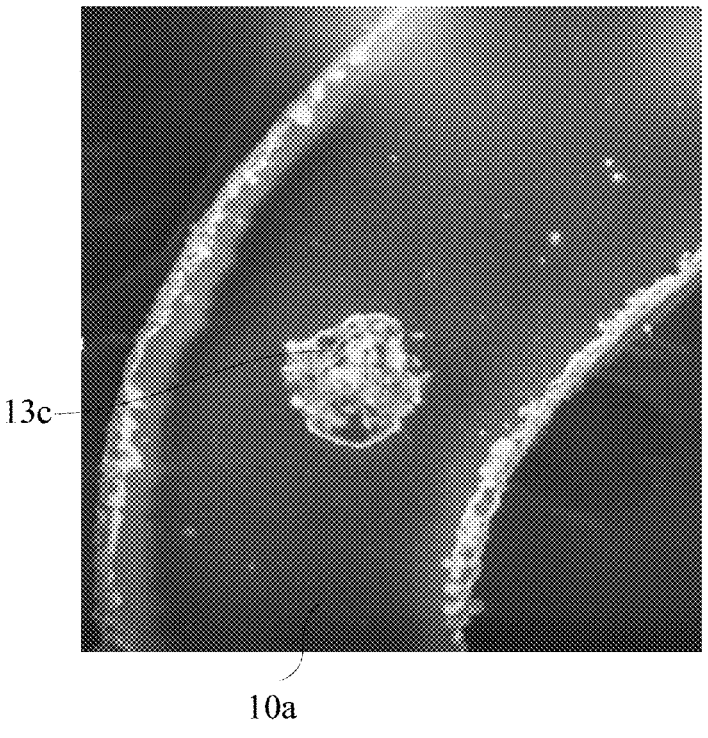

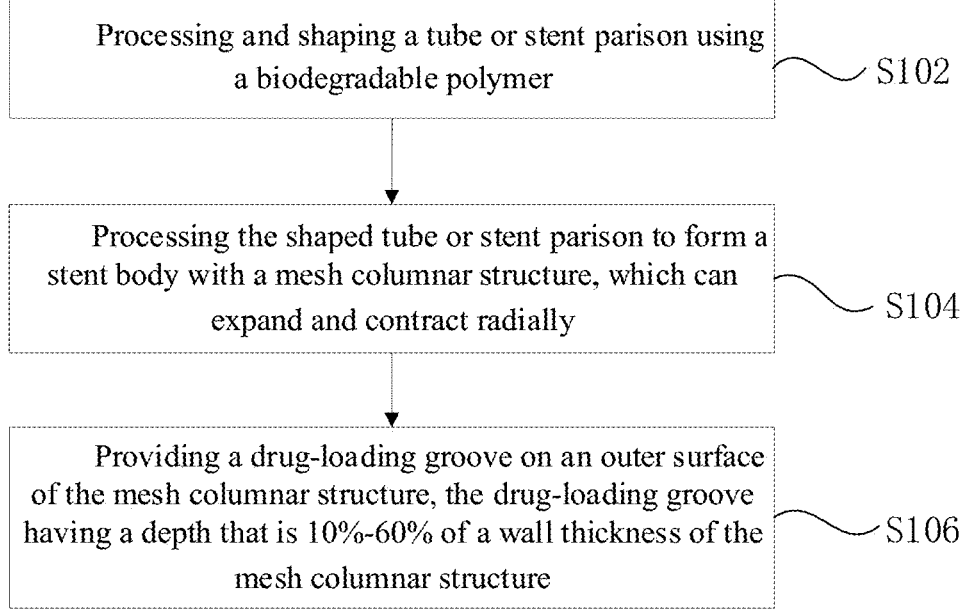

| | |
|---|---|
| Processing and shaping a tube or stent parison using a biodegradable polymer | S102 |
| Processing the shaped tube or stent parison to form a stent body with a mesh columnar structure, which can expand and contract radially | S104 |
| Providing a drug-loading groove on an outer surface of the mesh columnar structure, the drug-loading groove having a depth that is 10%-60% of a wall thickness of the mesh columnar structure | S106 |

DEGRADABLE DRUG-LOADED STENT AND MANUFACTURING METHOD THEREFOR

CROSS-REFERENCE OF RELATED APPLICATION

This application is a national stage of International Application No. PCT/CN2020/089349, filed on May 9, 2020, and entitled "DEGRADABLE DRUG-LOADED STENT AND MANUFACTURING METHOD THEREFOR", which claims priority benefit of Chinese patent application No. 201910389694.5, filed on May 10, 2019. The entireties of these applications are incorporated by reference herein for all purposes.

TECHNICAL FIELD

The present disclosure relates to the technical field of medical devices, in particular to a degradable drug-loading stent and a method for manufacturing the same.

BACKGROUND

Cardiovascular diseases have become one of the main diseases threatening human health. The most common diseases in cardiovascular diseases include coronary atherosclerotic heart disease, which is also often referred to as coronary heart disease. Coronary heart disease is a heart disease caused by myocardial ischemia and anoxia caused by stenosis or obstruction of blood vessel lumen induced by atheroma-like white plaques (called coronary atherosclerotic lesion) which are formed with lipids deposition in the blood on the originally smooth arterial intima due to abnormal lipid metabolism. Percutaneous arterial interventional stent surgery has become an important treatment for coronary heart disease. At present, the stents are of two main types: bare metal stents and drug-eluting stents. The biggest problem with bare metal stents is the possibility of intimal hyperplasia resulting in restenosis. The use of drug-eluting stents has reduced the restenosis rate to less than 10% compared to 30% for bare stents.

With the development of stent material technology, degradable stents have been widely used in drug-eluting stents due to their superior degradability, which allows their degradation and absorption after being implanted in a body for a period of time.

However, a few issues remain with the degradable stents. For example, during the process of coating the drug on the surface of the stent, the sprayed drug droplets are prone to overflow, resulting in inconsistent thickness and uneven distribution of the drug coating on the surface of the stent. After the stent is implanted into the body, the uneven distribution of the drug coating may cause uneven release of the drug or shedding of the part of the drug overflowed, which may easily cause thrombosis. In addition, the materials used in the degradable stents are more fragile than that used in metal stents. Based on this, it is urgently needed in the industry to overcome the practical technical problem of how to improve the adhesion of the drug on the stent while providing sufficient supporting force.

SUMMARY

Accordingly, the present disclosure provides a degradable drug-loading stent and a method for manufacturing the degradable drug-loading stent, improving the adhesion of drugs on the degradable stent while providing sufficient supporting force.

Provided is a degradable drug-loading stent, wherein the degradable drug-loading stent includes a stent body, and the stent body is provided with a drug-loading groove at an outer surface thereof, the stent body has a contracted state and an expanded state, the stent body is capable of being switched from the contracted state to the expanded state by radial expansion, the stent body has a mesh columnar structure in the expanded state, and the drug-loading groove has a depth that is 10% to 60% of a wall thickness of the mesh columnar structure.

Further, the stent body is made of biodegradable polymer.

Further, the depth of the drug-loading groove is 25% to 45% of the wall thickness of the mesh columnar structure.

Further, the depth of the drug-loading groove and a width of the drug-loading groove meet the following conditions: $Y=120-2X$; where Y is the depth of the drug-loading groove, X is the width of the drug-loading groove, and Y is in a range of less than or equal to 80 microns.

Further, the stent body includes a plurality of supporting unit rings and connecting rods, the supporting unit rings are connected by the connecting rods to form the mesh columnar structure, and the drug-loading groove is at least arranged on an outer surface of at least one of the supporting unit rings.

Further, a cumulative groove length of the drug-loading groove on at least one of the supporting unit rings is 0.9 to 5 times a length of the supporting unit ring where the drug-loading groove is located.

Further, a groove width of the drug-loading groove on at least one of the supporting unit rings is 10% to 80% of a width of the supporting unit ring where the drug-loading groove is located.

Further, at least one drug-loading groove on at least one of the supporting unit rings is made by continuous grooving.

Further, at least one of two supporting unit rings located at ends of the stent body is provided with a plurality of drug-loading grooves, the plurality of drug-loading grooves being arranged at intervals in a circumferential direction.

Further, at least one supporting unit ring located between the ends of the stent body is provided with a closed drug-loading groove.

Further, at least one of the supporting unit rings is provided with a plurality of the drug-loading grooves, the plurality of the drug-loading grooves being arranged at intervals along an axial direction of the supporting unit ring and not intersecting each other.

Further, a groove line of the drug-loading groove is a curved line or a wavy line extending along a circumferential direction of the supporting unit ring.

Further, the drug-loading groove on at least one of the supporting unit rings includes a plurality of convoluted groove sections and a plurality of connecting groove sections, two adjacent convoluted groove sections being connected by one connecting groove sections.

Further, the drug-loading groove on at least one of the supporting unit rings includes a plurality of sub-grooves, each of the sub-grooves respectively has a main body section and a circuitous section circuitously extending from an end of the main body section relative to the main body section, and the main body section extends in a circumferential direction of the at least one supporting unit ring, and a partial structure of the circuitous section and a partial structure of the main body section are arranged side by side at intervals.

Provided is a method for manufacturing a degradable drug-loading stent, wherein the method for manufacturing the degradable drug-loading stent includes:

processing and shaping a tube or stent parison using a biodegradable polymer;

processing the shaped tube or stent parison to form a stent body with a mesh columnar structure, the stent body being radially expandable and contractible;

providing a drug-loading groove on an outer surface of the mesh columnar structure, the drug-loading groove having a depth that is 10% to 60% of a wall thickness of the mesh columnar structure.

Further, during providing the drug-loading groove, a focal point of a femtosecond laser moves on the outer surface of the mesh columnar structure at a moving speed S meeting the following condition:

$$V < S \le 10V,$$

where V is a moving speed of the focal point of the femtosecond laser relative to the shaped tube or stent parison when the femtosecond laser processes the shaped tube or stent parison.

Further, a drug is filled into the drug-loading groove after providing the drug-loading groove.

Further, a surface of the stent body filled with the drug is polished.

The present disclosure provides a degradable drug-loading stent and a method for manufacturing the same. The stent body of the degradable drug-loading stent is made of a biodegradable polymer to realize biodegradation of the material-loading stent. By providing the drug-loading groove on the outer surface of the stent and filling the drug into the drug-loading groove, the adhesion of the drug to the stent body is improved, and the problem of uneven thickness distribution when the drug is adhered to the stent body in a coating manner is avoided. In addition, the depth of the drug-loading groove can be controlled to be 10% to 60% of the wall thickness of the mesh columnar structure, so as to meet the physical performance requirements of the degradable drug-loading stent while providing better adhesion effects for the drug.

BRIEF DESCRIPTION OF THE DRAWINGS

FIG. 18 is an electron micrograph of the inner surface of the stent body in the case where the drug-loading groove is provided on the supporting unit ring of the stent body, in which the energy concentration point of the drug-loading groove causes breakdown of the inner surface of the supporting unit ring; and FIG. 19 is a schematic flow chart of steps of a method for manufacturing a degradable drug-loading stent according to an embodiment.

DETAILED DESCRIPTION OF THE EMBODIMENTS

To make the present disclosure easy to understand, a more comprehensive description of the present disclosure will be given below with reference to the embodiments. Better embodiments of the present disclosure are given below. However, the present disclosure can be implemented in many different forms and shall not limited to the embodiments described herein. On the contrary, the purpose of providing these embodiments is to provide a more thorough and comprehensive understanding of the disclosure of the present disclosure.

It is to be noted that when an element is referred to as being "fixed to" another element, it may be located on the other element directly or with intervening elements therebetween. When an element is referred to as being "connected to" another element, it may be connected to the other element directly or with intervening elements therebetween. The "connection" also includes a detachable connection. The terms "upper", "lower", "left", "right", and the like used herein are just for the purpose of description, rather than indicating a unique embodiment.

Figure 1:
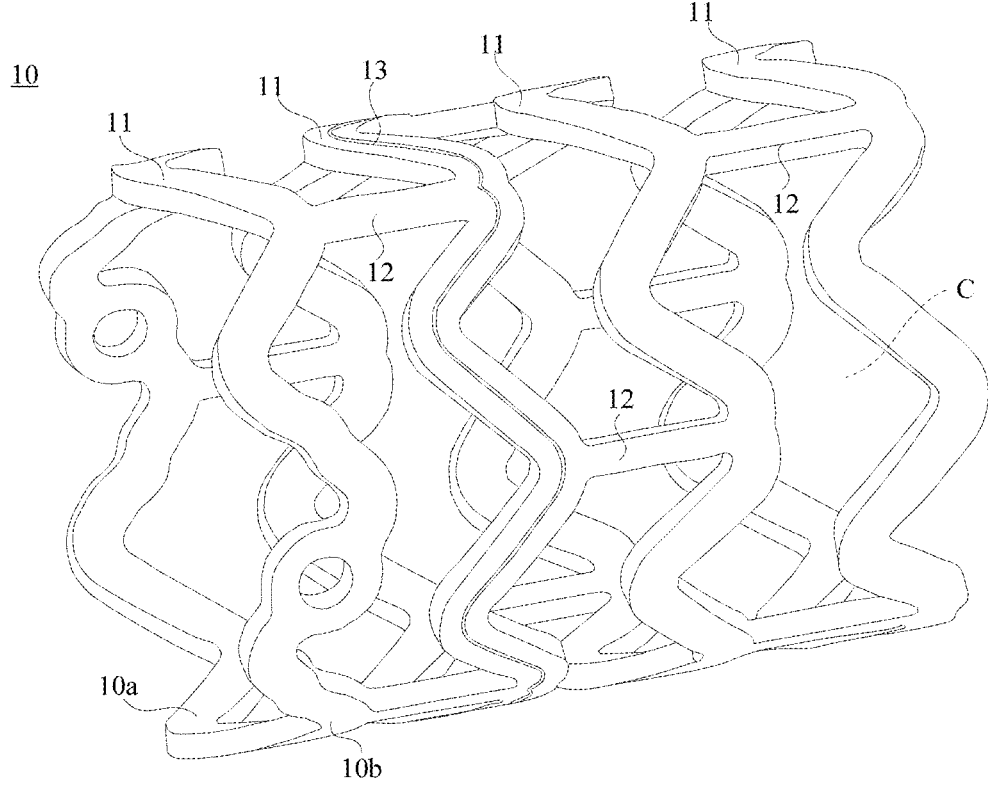
FIG. 1 is a schematic view of a stent body of a degradable drug-loading stent in an embodiment.
Figure 2:
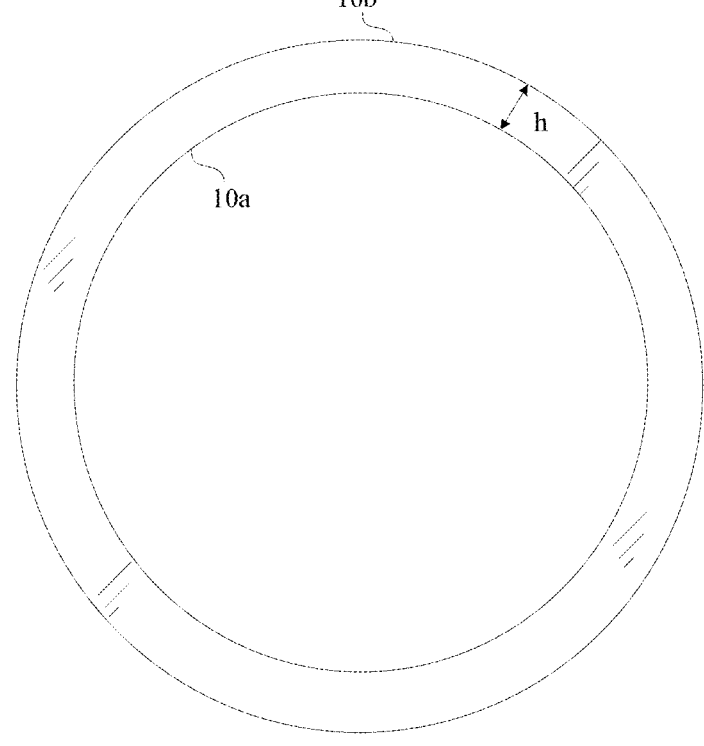
FIG. 2 is a schematic front view of the stent body of the degradable drug-loading stent shown in FIG. 1 along an axial direction.

As shown in FIGS. 1 and 2, a degradable drug-loading stent in an embodiment includes a stent body 10 made of a biodegradable polymer. The stent body 10 is made of a biodegradable polymer, thus can be degraded and absorbed after being put into a body, avoiding the problem that a conventional metal stent needs to be removed through a second operation which may cause negative effects. In this embodiment, the stent body 10 is a structure that can expand and contract radially, and has a contracted state and an expanded state. For example, the stent body 10 is in the contracted state when pressed on an outer surface of a balloon catheter, and changes to the expanded state after being expanded by a balloon catheter. A mesh columnar structure has opposite inner and outer surfaces 10a and 10b, wherein the outer surface 10b of the mesh columnar structure is provided with a drug-loading groove 13, and the drug-loading groove 13 has a depth that is 10% to 60% of a wall thickness of the mesh columnar structure. As shown in FIG. 2, the wall thickness h of the mesh columnar structure is a distance between the inner and outer surfaces 10a and 10b.

In this embodiment, the drug-loading groove 13 is provided on the outer surface 10b of the mesh columnar structure, so that the drug can be contained in the drug-loading groove 13, which can improve the adhesion of the drug to the degradable drug-loading stent, thereby reducing the probability of drug shedding, thus avoiding the uneven distribution of the drug on the outer surface of the stent body 10. When the depth of the drug-loading groove 13 is 10% to 60% of the wall thickness of the mesh columnar structure, the degradable drug-loading stent can also meet certain physical performance requirements. For example, the degradable drug-loading stent needs to meet the requirements of the radial anti-extrusion performance, over-expansion (OE for short) performance or axial retraction ability in criteria for medical devices. If the drug-loading groove 13 have a greater proportion of the wall thickness in the mesh columnar structure, the wall thickness of the degradable drug-loading stent would be thinner at the drug-loading groove 13 and easily fractured. By reasonably configuring the depth of the drug-loading groove 13, the stent body of the degradable drug-loading stent can not only meet the physical performance requirements and provide sufficient supporting force, but also provide better adhesion conditions for the drug and improve the adhesion effect of the drug.

In some embodiments, the stent bodies of several degradable drug-loading stents shown in FIG. 1 are selected for physical performance testing. The stent bodies of several degradable drug-loading stents used in the test are roughly divided into four types as shown in Table 1. The different types of degradable drug-loading stents have basically the same structural design and size of the stent body except for the depth of the drug-loading groove 13. Specifically, the test results are shown in Table 1.

TABLE 1

| Wall thickness of mesh columnar structure | Depth of drug-loading groove | Proportion of groove depth | Mean Supporting force | Mean OE |
|---|---|---|---|---|
| 125 μm | 38.84 μm | 31.07% | 87.29 Kpa | 5.28 mm |
| 125 μm | 45.26 μm | 36.21% | 76.88 Kpa | 5.19 mm |
| 125 μm | 75.27 μm | 60.02% | 50.08 Kpa | 5.17 mm |
| 125 μm | 84.56 μm | 67.64% | 49.6 Kpa | 5.21 mm |

In Table 1, all the mesh columnar structures of the degradable drug-loading stents have the wall thickness of 125 μm. By only adjusting the depth of the drug-loading groove 13, corresponding proportions of groove depth of different types of degradable drug-loading stents are 31.07%, 36.21%, 60.02%, and 67.64%, respectively. Among them, the proportion of groove depth refers to the ratio of the depth of the drug-loading groove 13 to the wall thickness h of the mesh columnar structure. The stent bodies of the degradable drug-loading stents with the proportions of groove depth of 31.07%, 36.21%, 60.02%, and 67.64% were tested for supporting force and over-expansion, and the corresponding mean values were obtained through multiple tests. It is found that the mean supporting force of the degradable drug-loading stents with the proportions of groove depth of 31.07%, 36.21%, and 60.02% is not less than 50 Kpa, which meets the criteria for the degradable drug-loading stents supporting in the body. Correspondingly, the degradable drug-loading stent with the proportion of groove depth of 67.64% has a measured mean supporting force of 49.6 Kpa which is slightly less than the specified 50 Kpa, and is determined to be unqualified since the insufficient supporting force may cause a risk of collapse in the body. Table 1 also shows that when the proportion of groove depth varies at 31.07%, 36.21%, 60.02%, and 67.64%, all the mean over-expansions of the corresponding degradable drug-loading stents (mean over-expansion size of the stent bodies of the several degradable drug-loading stents after the over-expansion test) change very little and are 4.5 mm or more, which meets the expansion performance standard of the degradable drug-loading stent.

It should be noted that Table 1 shows the results of supporting force and over-expansion performance tests performed on the stent bodies of the several degradable drug-loading stents with proportion of groove depth of 31.07%, 36.21%, 60.02%, and 67.64%, respectively. It reflects that the proportion of groove depth has a greater influence on the supporting force of the degradable drug-loading stent, but has a smaller influence on the over-expansion performance. Further, in order to make the drug-loading grooves 13 of the different types of degradable drug-loading stents have substantially the same drug-loading capacity, that is, to make the volumes of the different types of drug-loading grooves 13 substantially the same, it is necessary to adapt the groove width of the drug-loading groove 13 as the depth of the drug-loading groove 13 changes. Among them, the smaller the proportion of groove depth of the drug-loading groove 13 relative to the mesh columnar structure, the shallower the drug-loading groove 13. Thus, the groove width of the drug-loading groove 13 needs to be widened or the number of the drug-loading groove 13 needs to be increased in order to increase a ratio of the grooved area to the area of the outer surface 10b of the mesh columnar structure. In other words, the groove depth cannot be reduced infinitely while maintaining the drug-loading capacity of the drug-loading groove 13 so as to allow the drug to be well adhered to the drug-loading groove 13. If the proportion of groove depth is too small, the ratio of the grooved area to the area of the outer surface 10b of the mesh columnar structure would be too large, which will easily lead to a thinner edge structure, thus a lower strength, of the drug-loading groove 13, resulting in easy cracking.

During the research of reducing the proportion of groove depth, the inventor found that when the proportion of groove depth is reduced to less than 10%, the width of the groove would be widened in order to ensure sufficient drug-loading space, leading to a thinner edge structure of the drug-loading groove, resulting in easy cracking during the expansion test. Then, the overall mechanical performance of the stent body of the degradable drug-loading stent decreases. Accordingly, as verified by experiments, it is reasonable and safe to control the depth of the drug-loading groove 13 to account for 10% to 60% of the wall thickness of the mesh columnar structure considering that the degradable drug-loading stent can provide sufficient supporting force and the ability of the drug to be adhered to the stent body.

In some embodiments, the depth of the drug-loading groove 13 can be controlled to account for 25% to 45% of the wall thickness h of the mesh columnar structure. As verified by experiments, the depth and width of the drug-loading groove 13 corresponding to this range can better meet the processing requirements in the case where the drug-loading capacity is the same. For example, in the case where a laser beam emitted by a femtosecond laser is employed to process the drug-loading groove 13 on the outer surface 10b of the mesh columnar structure, if the processing width of a single scan of the laser beam is φ, controlling the width of the drug-loading groove 13 roughly at φ may avoid repeated laser processing. Then, the laser beam is only required to move along a processing path to form the drug-loading groove 13 adapted to the processing path.

In some embodiments, in order to meet the requirement of drug-loading capacity, the depth and the width of the drug-loading groove 13 meet the following conditions, for example: $Y=120-2X$, where Y is the groove depth, X is the groove width, and Y is in a range of less than or equal to 80 microns and, obviously, greater than zero. When the groove depth and groove width meet the above conditions, an excessive groove depth which affects the mechanical properties of the biodegradable polymer stent can be avoided, and the drug-loading requirements of the medical stent can also be met.

There are many options for the biodegradable polymer of which the stent body 10 is made.

In some embodiments, the biodegradable polymer includes one or more of the following substances: polylactic acid (PLA), poly-L-lactic acid (PLLA), polyglycolide or polyglycolic acid, PGA, polycyanoacrylate (PACA), poly-caprolactone (PCL), polyanhydrides, polylactic acid copolymer (PLGA), polyhydroxybutyrate valerate (PHBV), polyacetylglutamic acid (PAGA), polyorthoester (POE), polyoxyethylene/polybutylene copolymer (PEO/PBTP), polyorthoester, polycaprolactone, polyglycolic acid, polyoxyethylene/polybutylene terephthalate copolymer, methacrylate salt or ester, methacrylate salt or ester, polyurethane, silicone, polyvinyl alcohol, vinyl alcohol, polyglycolic acid, polyphosphatase, and copolymers or blends formed with at least two of the monomers of the above-mentioned polymers.

In some embodiments, the drug filled in the drug-loading groove 13 includes one or more of the following substances: anti-inflammatory drugs, antiplatelet drugs, anticoagulants, anticancer drugs, immunosuppressants and/or hormones, intimal cell proliferation inhibitor. The drug filled in the drug-loading groove 13 is preferably one or more of rapamycin and derivatives thereof, paclitaxel and derivatives thereof, probucol and derivatives thereof, dexamethasone and derivatives thereof, asiaticoside, heparin, aspirin, cilostazol, ticlopidine, triptolide, cyclosporine, tacrolimus, or estradiol. The drug filled in the drug-loading groove 13 is more preferably rapamycin.

Continuing to refer to FIG. 1, the stent body 10 includes a plurality of supporting unit rings 11 and connecting rods 12. The supporting unit rings 11 are connected by the connecting rods 12 to form the mesh columnar structure. The drug-loading groove 13 is preferably located on the supporting unit ring 11.

Figure 3:
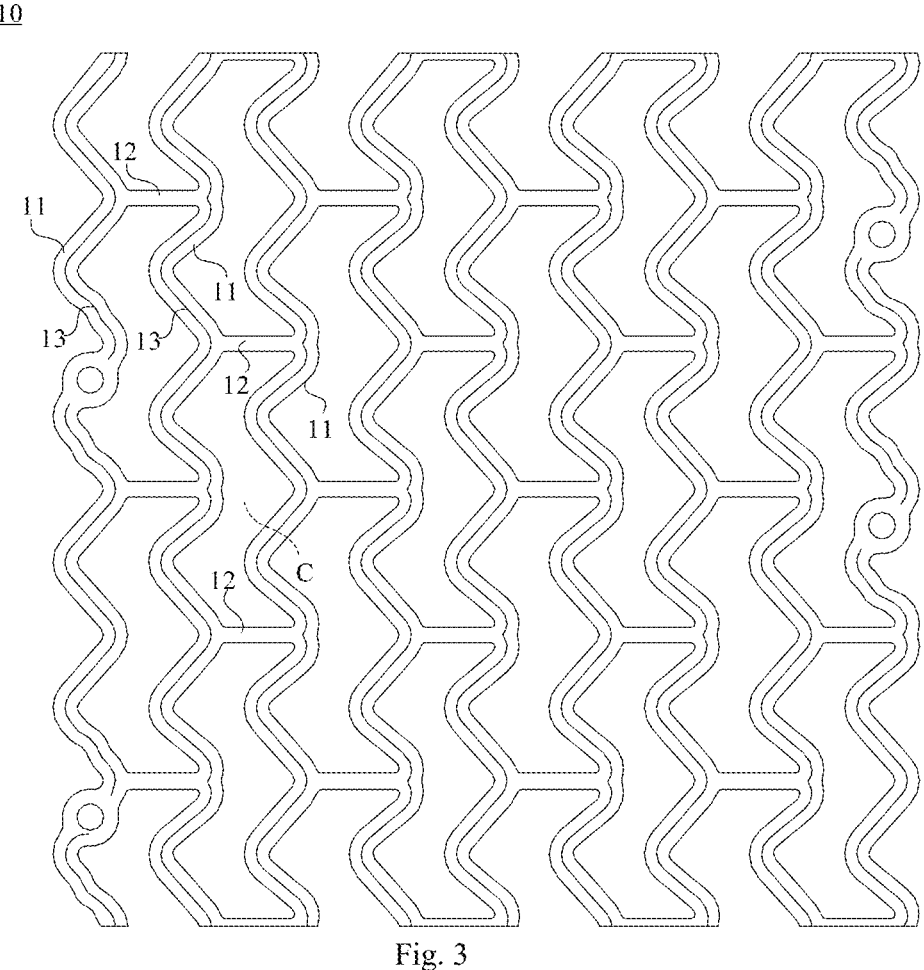
FIG. 3 is a schematic deployment view of the stent body of the degradable drug-loading stent shown in FIG. 1.
Figure 4:
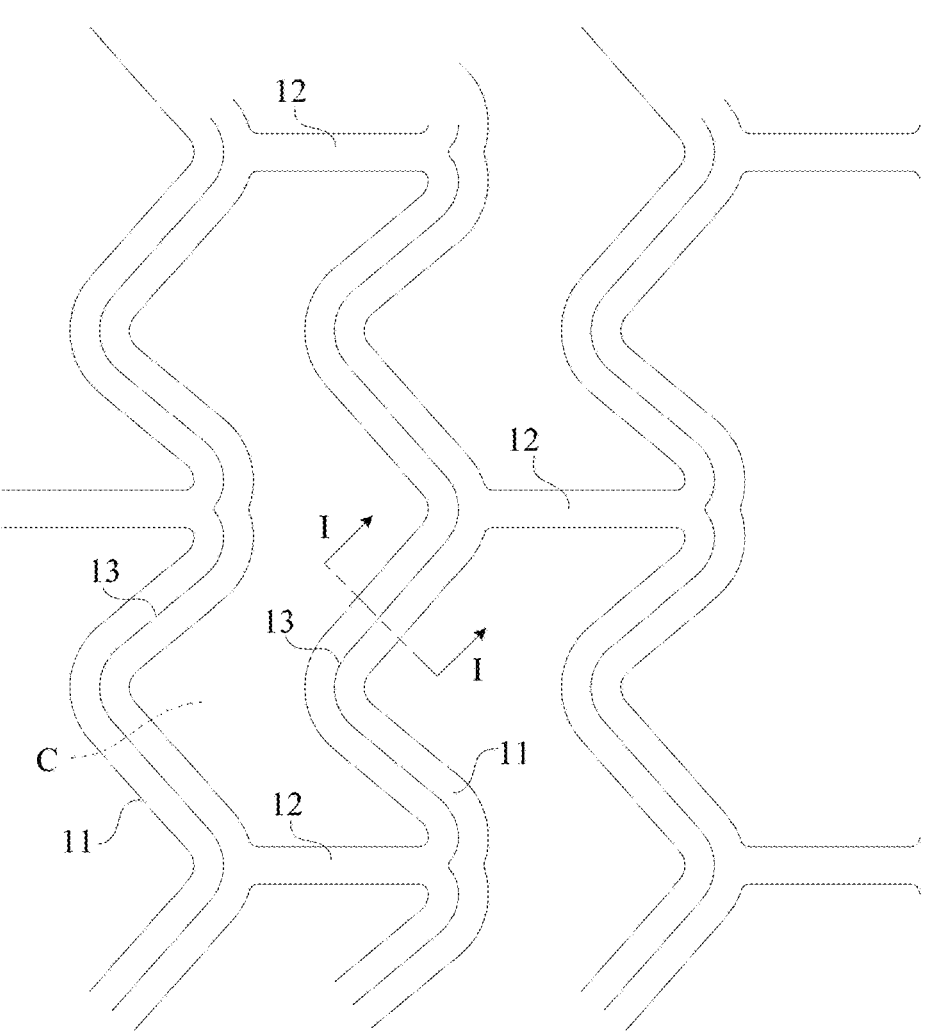
FIG. 4 is a partial schematic view of the stent body of the degradable drug-loading stent shown in FIG. 3.

As shown in FIGS. 3 and 4, in some preferred manners, at least one drug-loading groove 13 on at least one of the supporting unit rings 11 is made by continuous grooving. Preferably, the drug-loading grooves 13 on each of the supporting unit rings 11 form a continuous groove made by continuous grooving. The drug-loading groove 13 formed by continuous grooving can be understood as, for example, that a grooving tool (such as laser) is not interrupted or paused during the grooving process, so that there is no energy concentration point on the groove section between the two ends of the drug-loading groove 13 (for instance if the laser focus point pauses during processing, the energy will be concentrated and superimposed at the pause point, which would forms an energy concentration point with a deeper groove depth). For example, in FIG. 3, each drug-loading groove 13 on the supporting unit rings 11 at both ends of the stent body 10 has two ends, one of which corresponds to a position of a starting point for grooving, and the other corresponds to a position of an ending point for grooving. Taking the laser processed and shaped drug-loading groove 13 as an example, when processing the drug-loading groove 13, the laser continuously emits light with the focus point of the laser moving from the position of the starting point for grooving to the position of the ending point at a constant cutting speed as set, so that the drug-loading groove 13 is processed and shaped in one step by continuous grooving. In this way, the number of energy concentration points of the drug-loading groove 13 on the supporting unit ring 11 can be minimized under the same groove length, that is to say, the probability of material breakdown due to the concentration of laser energy at the energy concentration point is reduced. This structural form can not only provide a greater drug-loading capacity, but also reduce material loss due to breakdown, preventing the stent body 10 from generating local stress due to the material loss, thereby reducing the risk of fracture of the stent body 10.

In some embodiments, the two ends of the drug-loading groove 13 overlap so that a groove line of the drug-loading groove 13 is closed. For example, the positions of the starting point and the ending point for grooving of the drug-loading groove 13 overlap, so that the drug-loading groove 13 forms a closed loop (for example in FIG. 3, the drug-loading groove 13 on the supporting unit ring 11 in the middle may be a closed-loop groove). In this embodiment, the drug-loading groove 13 is a continuous groove which may be formed by one step continuous processing and shaping instead of multiple processing and shaping in sections, so as to minimize the number of energy concentration points of the drug-loading groove 13 on the supporting unit ring 11. As mentioned above, when the drug-loading groove 13 is processed by laser, the laser energy tends to produce a superimposed effect at the pause position or the interrupted position and break down the stent body 10 made of the biodegradable polymer. Therefore, processing the drug-loading groove 13 by this continuous grooving method can reduce the breakdown probability of the stent body 10 and minimize the number of stress points of the stent body 10, thereby maintaining good physical properties of the degradable drug-loading stent.

Figure 15:
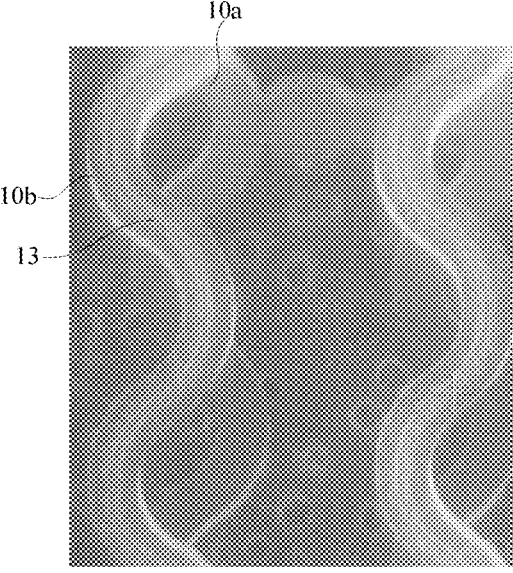
FIG. 15 is an electron micrograph of an outer surface of a degradable drug-loading stent according to an embodiment when a continuous drug-loading groove is provided on a supporting unit ring of a stent body.
Figure 16:
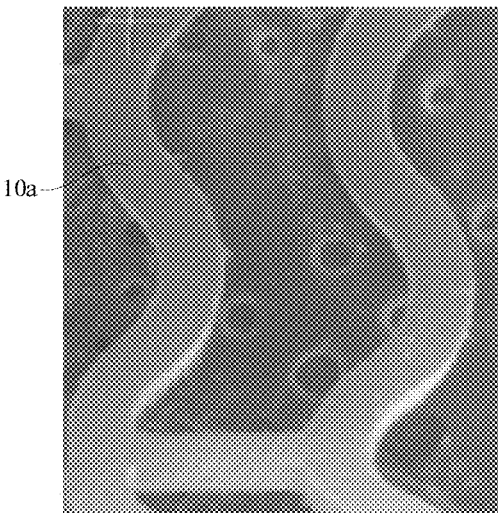
FIG. 16 is an electron micrograph of an inner surface of the stent body in the case where the continuous drug-loading groove is provided on the supporting unit ring of the stent body shown in FIG. 15.
Figure 17:
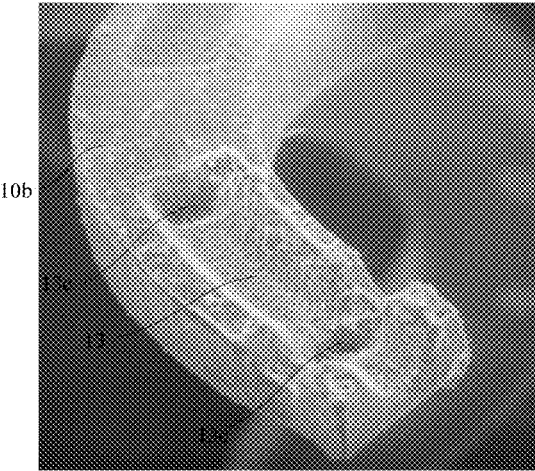
FIG. 17 is an electron micrograph of a drug-loading groove provided on a supporting unit ring of a stent body according to an embodiment, which shows that a groove depth of an energy concentration point of the drug-loading groove is relatively deep.

As shown in FIGS. 15 and 16, FIG. 15 shows the groove sections at the non-end part of the drug-loading groove 13 formed by continuous grooving, and FIG. 16 shows that there is no breakdown point on the side of the inner surface 10*a*. As shown in FIGS. 17 and 18, at the energy concentration point 13*c* of the drug-loading groove 13 which, for example, is caused by the superposition of laser energy caused by the pause, the depth of the energy concentration point 13*c* is deeper than that of the non-pause point of the continuously processed drug-loading groove 13, and the breakdown phenomenon is likely to occur at the energy concentration point (see FIG. 18). Thus a breakdown point where a local material stress would be formed is easy to form on the side of the inner surface 10*a* and is not conducive to the structural strength of the stent body 10. It can be seen from the above-mentioned embodiments that the use of continuous laser grooving to form the drug-loading groove 13 with continuous groove lines can reduce this breakdown phenomenon and can maintain the good physical properties of the degradable drug-loading stent.

In some embodiments, two adjacent ends of two adjacent drug-loading grooves 13 are arranged at an interval, so as to further avoid the superimposition of the laser energy on the two overlapping ends and easy breakdown of supporting unit ring 11 when the drug-loading groove 13 is processed by laser. This structural form reduces the risk of the supporting unit ring 11 being broken down, thereby preventing the stent body 10 from being fractured due to stress concentration at the brokendown position when the stent body 10 contracts or expands.

In some embodiments, each supporting unit ring 11 is provided with a plurality of drug-loading grooves 13 to increase the drug-loading capacity.

It should be noted that the structural configurations of the supporting unit ring 11 has many possibilities. For example, in some embodiments, the supporting unit ring 11 may be a ring structure formed by one supporting rod. For another example, in some embodiments, the supporting unit ring 11 may be a mesh ring structure formed by a plurality of supporting rod. The structural configuration of the supporting unit ring is not limited herein.

Figure 11:
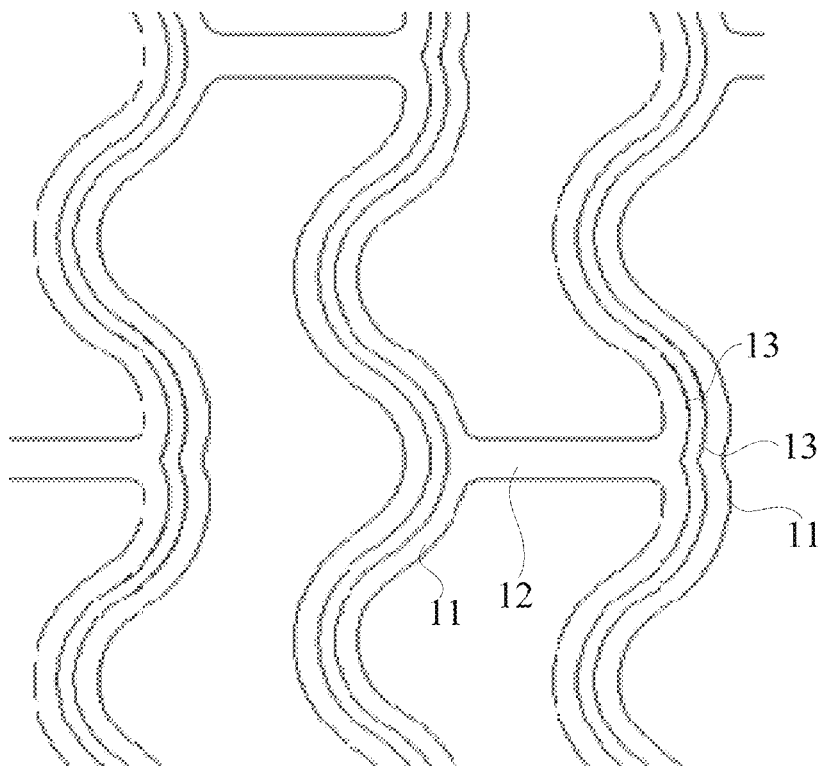
FIG. 11 is a partial schematic view of a stent body of a degradable drug-loading stent according to another embodiment when it is deployed.

In addition, in the case where the drug-loading groove 13 is provided on the surface of the supporting unit ring 11, the extending direction and the arrangement form of the drug-loading grooves 13 can be adjusted adaptively according to the supporting rods constituting the supporting unit ring 11. For example, in some embodiments, the supporting unit ring 11 is constituted by the supporting rods. When a plurality of drug-loading grooves 13 are provided, the plurality of drug-loading grooves 13 are arranged at intervals along the axial direction of the supporting unit ring 11 and do not intersect each other, thereby avoiding the superimposition of laser energy at the intersection which may cause the stent body 10 to easily produce breakdown points. As shown in FIG. 11, each supporting unit ring 11 is provided with two drug-loading grooves 13 with each having substantially the same profile in the extending direction, that is, the two drug-loading grooves 13 are substantially equal in each interval therebetween in the extending direction, and extend substantially parallel to each other, so that the two drug-loading grooves 13 are uniformly distributed on the surface of the supporting unit ring 11, and the supporting unit ring 11 has equivalent physical properties of the materials everywhere, and more balanced forces, and better overall structural strength.

On this basis, when the supporting unit ring 11 is constituted by a plurality of supporting rods, the drug-loading grooves 13 provided on the plurality of supporting rods can also be grooved according to the extending direction of each supporting rod in addition to continuous and non-intersecting grooving to obtain the overall better physical and mechanical properties of the degradable drug-loading stent. For example, the groove line of the drug-loading groove 13 on each supporting rod has a direction roughly the same as that of the supporting rod, so that the force on each place is equivalent and local stress and easy fracture is avoided after the supporting rod is grooved.

Figure 12:
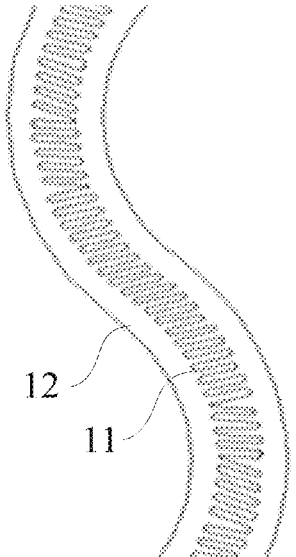
FIG. 12 is a schematic view of a configuration of a drug-loading groove on a supporting unit ring of the stent body in the degradable drug-loading stent according to another embodiment.

As shown in FIG. 12, in some embodiments, the groove line of the drug-loading groove 13 may also be a curved line or a wavy line extending along the circumferential direction of the supporting unit ring 11 to increase a cumulative groove length per unit length along the extending direction of the supporting unit ring 11, thereby increasing the drug-loading capacity.

Figure 5:
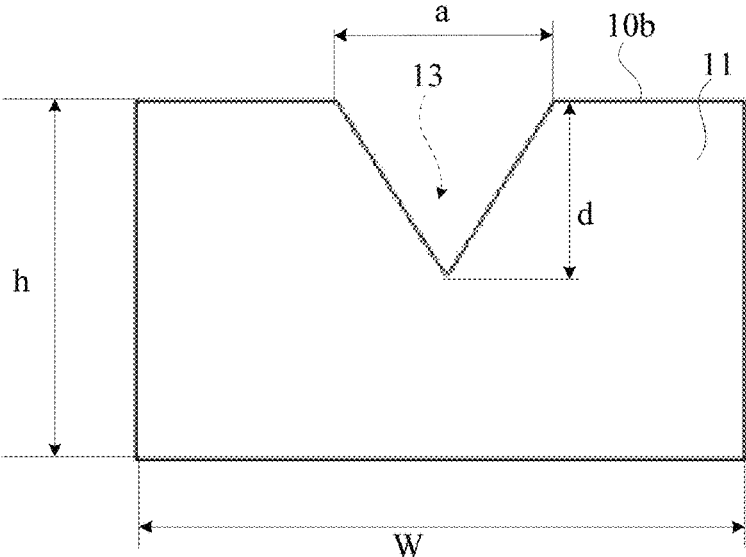
FIG. 5 is a schematic cross-sectional view of the stent body of the degradable drug-loading stent shown in FIG. 4 along a line I-I.
Figure 6:
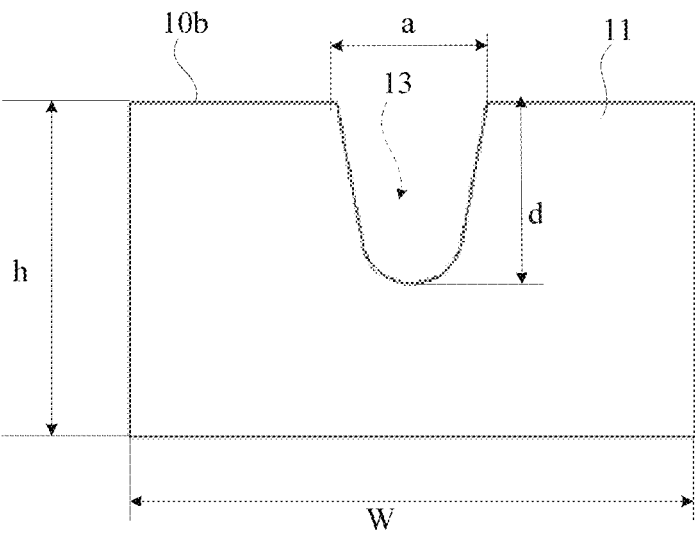
FIG. 6 is a schematic cross-sectional view of another embodiment when the stent body of the degradable drug-loading stent shown in FIG. 4 is cross-sectionally viewed along the line I-I.
Figure 7:
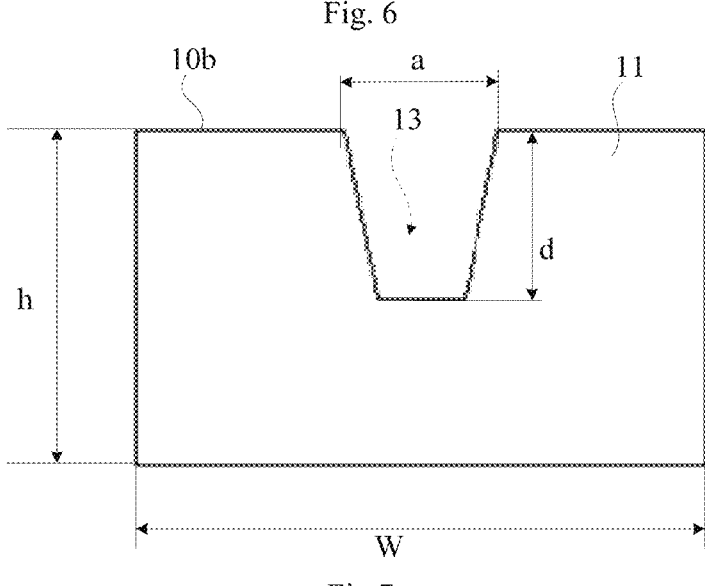
FIG. 7 is a schematic cross-sectional view of yet another embodiment when the stent body of the degradable drug-loading stent shown in FIG. 4 is cross-sectionally viewed along the line I-I.
Figure 8:
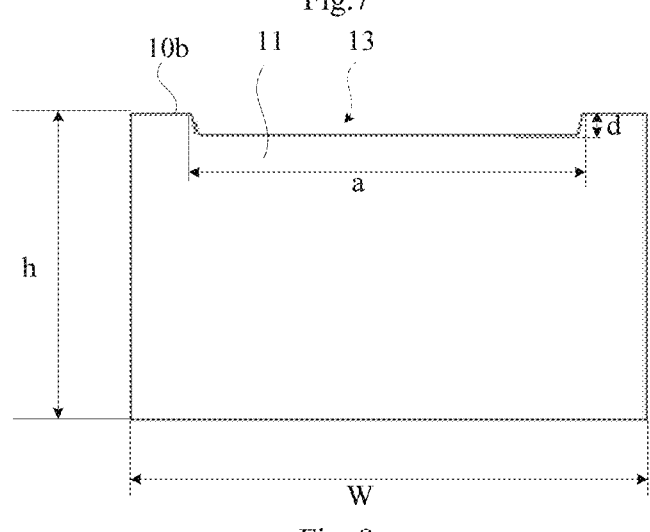
FIG. 8 is a schematic cross-sectional view of still another embodiment when the stent body of the degradable drug-loading stent shown in FIG. 4 is cross-sectionally viewed along the line I-I.

The drug-loading groove 13 may have a variety of possible cross-sectional shapes. For example, the cross-sectional shape of the drug-loading groove 13 is V-shaped, as shown in FIG. 5. The cross-sectional shape of the drug-loading groove 13 is U-shaped, as shown in FIG. 6. The cross-sectional shape of the drug-loading groove 13 is trapezoidal, as shown in FIGS. 7 and 8. As shown in FIGS. 5 to 8, the depth d (equivalent to the above groove depth Y) and the width a (equivalent to the above groove width X) of the drug-loading groove 13 can be adjusted adaptively to meet different drug-loading requirements, as long as satisfied that the depth d of the drug-loading groove 13 is 10% to 60% of the wall thickness h of the mesh columnar structure.

In some embodiments, the width a of the drug-loading groove 13 is 10% to 80% of the width W of the supporting unit ring 11. In the case of maintaining the drug-loading capacity unchanged, the larger the width a of the drug-loading groove 13 is, the smaller the depth d of the drug-loading groove 13 is. That is to say, when designing the defining size of the drug-loading groove 13, the wider the width a of the drug-loading groove 13 is designed, the shallower the depth of the drug-loading groove 13 is in order to meet the predetermined drug-loading requirement.

Figure 9:
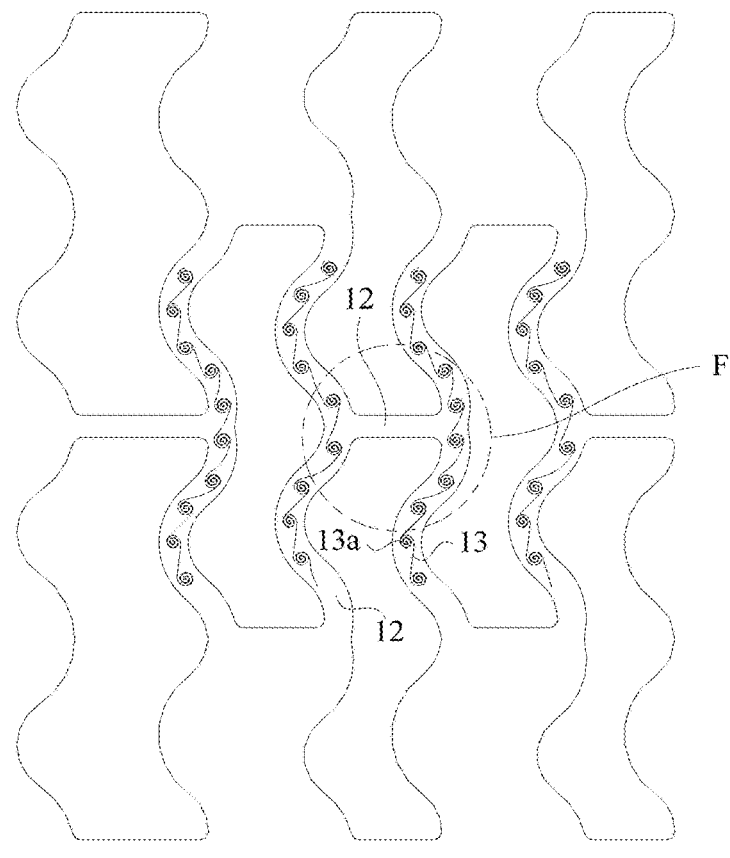
FIG. 9 is a partial schematic view of a stent body of a degradable drug-loading stent according to another embodiment when it is deployed.

In some embodiments, the cumulative groove length of the drug-loading groove 13 is 0.9 to 5 times the length of the supporting unit ring 11 where the drug-loading groove is located. Thus, the drug-loading capacity can be increased by providing a longer drug-loading groove 13. In the case where the drug-loading groove 13 is a continuous groove, the cumulative groove length of the drug-loading groove 13 can be 0.9 to 5 times the length of the supporting unit ring 11 where the drug-loading groove is located by circuitous grooving or spiral grooving. For example, as shown in FIG. 9, the overall extending direction of the drug-loading groove 13 is consistent with the extending direction of the supporting unit ring 11, the grooving paths of the drug-loading groove 13 do not intersect, and continuous grooving is used as much as possible to form a continuous groove, avoiding the occurrence of breakdown points due to energy concentration at the intersection position or the pause position. By spiral or circuitous grooving, the cumulative length of the drug-loading groove 13 is less limited by the length of the supporting unit ring 11, and can be 5 times the length of the supporting unit ring 11 where the drug-loading groove is located, so as to increase the drug-loading capacity. By continuous grooving, the phenomenon of material breakdown is less occurred, so that the better physical properties of the degradable drug-loading stent can be maintained to meet the requirements of use.

Figure 10:
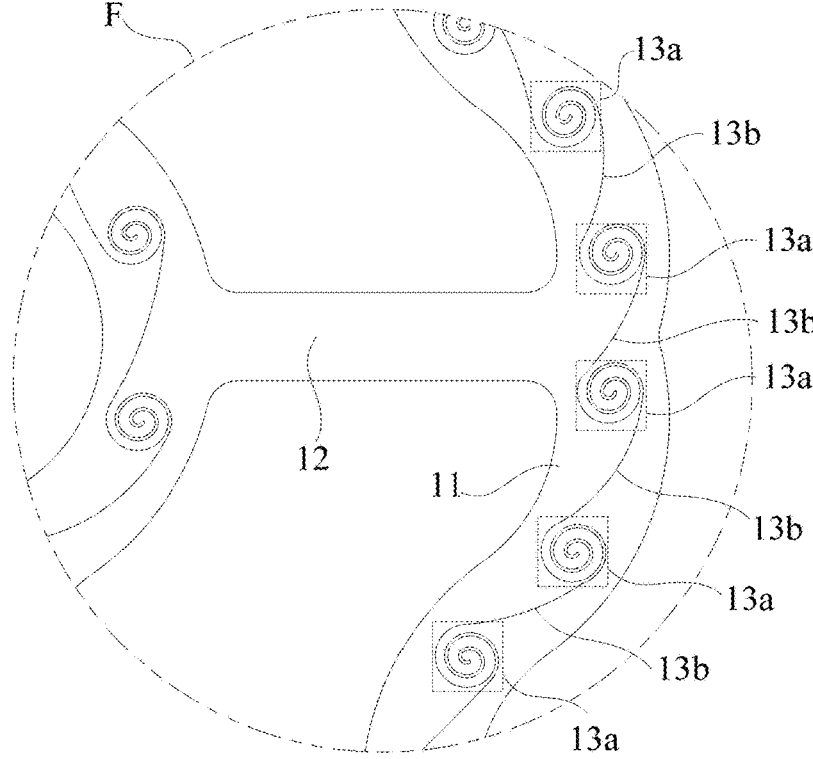
FIG. 10 is a partial enlarged schematic view of the part circled F in FIG. 9.

As shown in FIGS. 9 and 10, the drug-loading groove 13 includes a convoluted groove section 13*a* and a connecting groove section 13*b*. Preferably, on the same supporting unit ring 11, the cumulative groove length of the convoluted groove section 13a is greater than the length of the connecting groove section 13b, and the groove lines of the convoluted groove section 13a do not intersect each other. In this embodiment, the convoluted groove section 13a has a denser groove line than the connecting groove section 13b, so that the convoluted groove section 13a can be used to increase the local drug-loading capacity to perform site-specific drug administration. To be precise, since the cumulative groove length of the convoluted groove section 13a is greater than the length of the connecting groove section 13b on the same supporting unit ring 11, the amount of drug loaded in the convoluted groove section 13a is relatively large, which can prolong the medicinal effect at the site corresponding to the convoluted groove section 13a after the degradable drug-loading stent is loaded with drugs and implanted in the body.

The drug-loading groove 13 includes a plurality of convoluted groove sections 13a and a plurality of connecting groove sections 13b, and the plurality of convoluted groove sections 13a are connected in series by the plurality of connecting groove sections 13b, so that the drug-loading groove 13 can be obtained by continuous grooving as far as possible to minimize the possibility of breakdown due to energy concentration at a local location, thereby improving the overall structural strength of the degradable drug-loading stent to maintain better physical properties of the stent body 10.

The distances between the plurality of convoluted groove sections 13a can be equal, in other words, the plurality of convoluted groove sections 13a can be evenly distributed on the corresponding supporting unit ring 11, so that the force on each position of the supporting unit ring 11 is balanced and a relatively stable structural strength is maintained.

Figure 13:
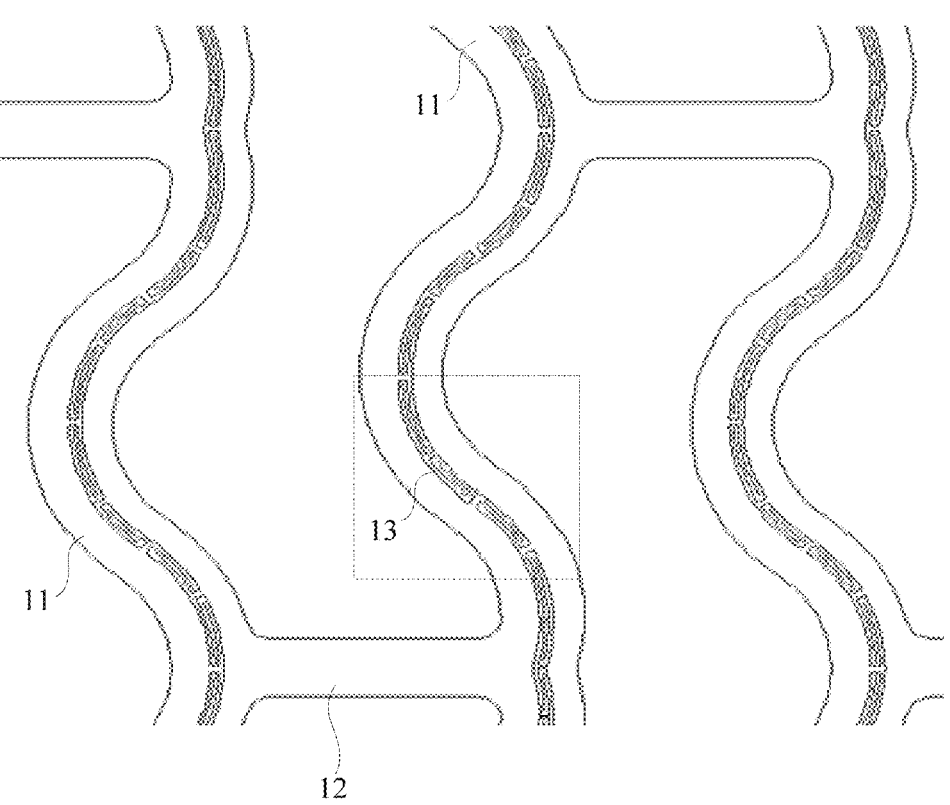
FIG. 13 is a partial schematic view of a stent body of a degradable drug-loading stent according to another embodiment when it is deployed.
Figure 14:
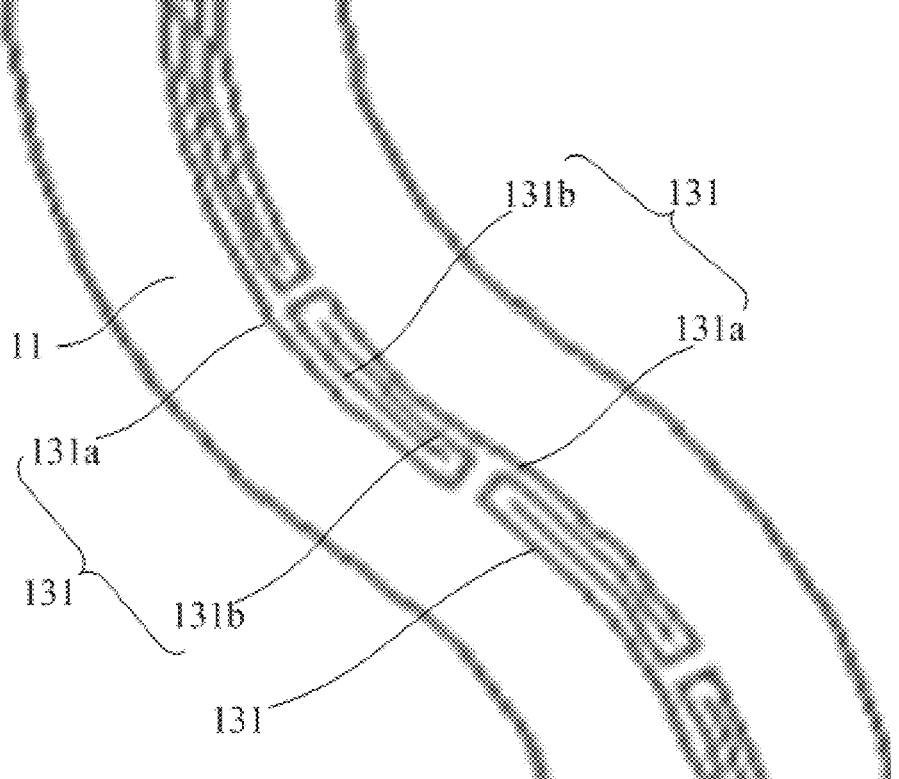
FIG. 14 is a partial enlarged schematic view of the dashed frame in FIG. 13.

As shown in FIGS. 13 and 14, in some embodiments, the drug-loading groove 13 can also increase the cumulative groove length per unit length on the supporting unit ring 11 in a circuitous way, so as to load more drug.

Specifically, the drug-loading groove 13 includes a plurality of sub-grooves 131, each of the sub-grooves 131 respectively has a main body section 131a and a circuitous section 131b circuitously extending from an end of the main body section 131a toward the opposite direction relative to the main body section 131a. The main body section 131a extends in the circumferential direction of the supporting unit ring 11, and the partial structure of the circuitous section 131b and the partial structure of the main body section 131a are arranged side by side at intervals. This circuitous arrangement increases the cumulative groove length per unit length in the extending direction of the supporting unit ring 11 to meet the requirement for loading more drugs. It should be pointed out that in this embodiment, the adjacent sub-grooves 131 are nested together through their respective circuitous sections 131b, and the groove lines of the multiple sub-grooves 131 do not intersect each other, so as to avoid the possibility of breakdown due to energy concentration at the intersection of the groove lines when processing the drug-loading groove 13 by laser.

On the other hand, as shown in FIG. 19, the present disclosure also provides a method for manufacturing a degradable drug-loading stent, the method for manufacturing the degradable drug-loading stent includes:

Step S102, a tube or stent parison is processed and shaped using a biodegradable polymer.

Among them, the biodegradable polymer includes one or more of the following substances: polylactic acid (PLA), poly-L-lactic acid (PLLA), polyglycolide or polyglycolic acid, PGA, polycyanoacrylate (PACA), polycaprolactone (PCL), polyanhydrides, polylactic acid copolymer (PLGA), polyhydroxybutyrate valerate (PHBV), polyacetylglutamic acid (PAGA), polyorthoester (POE), polyoxyethylene/polybutylene copolymer (PEO/PBTP), polyorthoester, polycaprolactone, polyglycolic acid, polyoxyethylene/polybutylene terephthalate copolymer, methacrylate salt or ester, methacrylate salt or ester, polyurethane, silicone, polyvinyl alcohol, vinyl alcohol, polyglycolic acid, polyphosphatase, and copolymers or blends formed with at least two of the monomers of the above-mentioned polymers. The tube or stent parison processed and shaped using the biodegradable polymer can be degraded in vivo and does not need to be removed by surgery.

Step S104, the shaped tube or stent parison is processed using a femtosecond laser to form a stent body 10 with a mesh columnar structure, which can expand and contract radially.

As shown in FIGS. 1 and 3, for the shaped tube or stent parison, the femtosecond laser is used to process and remove part of the material to provide a hollow groove C, thereby forming a radially expandable mesh columnar structure, that is, the stent body 10.

Step S106, a drug-loading groove is provided on an outer surface of the mesh columnar structure using the femtosecond laser, and the drug-loading groove has a depth that is 10% to 60% of a wall thickness of the mesh columnar structure.

In some embodiments, when processing the drug-loading groove 13, the laser continuously emits light with the focal point of the laser moving from the position of the starting point for grooving to the position of the ending point. For the unclosed drug-loading groove 13, the position of the starting point and the position of the ending point preferably correspond to one end and the other end of one continuous drug-loading groove 13, so that the number of energy concentration points of the drug-loading groove 13 on the supporting unit ring 11 can be minimized under the same groove length, that is to say, the phenomenon of material breakdown due to the concentration of laser energy at a local location is reduced. This structural form can not only provide a greater drug-loading capacity, but also reduce breakdown point, thereby preventing the stent body 10 from generating local stress due to the material loss, and reducing the risk of fracture of the stent body 10.

In some embodiments, during providing the drug-loading groove 13 using the femtosecond laser, a focal point of the femtosecond laser moves on the outer surface of the mesh columnar structure at a moving speed S meeting the following condition:

$$V < S \le 10V,$$

where V is a moving speed of the focal point of the femtosecond laser relative to the shaped tube or stent parison when the femtosecond laser processes the shaped tube or stent parison.

In this embodiment, during providing the drug-loading groove 13 using the femtosecond laser, the focal point of the femtosecond laser moves on the outer surface 10b of the mesh columnar structure at a speed faster than the cutting speed during processing the hollow groove in the shaped tube or stent parison. That is to say, the laser cutting speed for opening the drug-loading groove 13 is faster than the laser cutting speed for providing the hollow groove C, so as to reduce the laser energy absorbed per unit cutting length and reduce the risk of breakdown of the stent body 10.

After finishing the processing of the drug-loading groove, a drug is filled into the drug-loading groove 13 in a micron-level or nano-level spraying manner. After the drug filling is finished, a surface of the stent body can be polished to remove the drugs overflowing the surface of the stent. The thickness of the drug contained in the drug-loading groove 13 everywhere is basically uniform, and the drug can be uniformly released.

For the degradable drug-loading stent of the present disclosure in which the drug-loading groove 13 is provided on the stent body 10 made of biodegradable polymer, the drug-loading groove 13 allows the adhesion ability of the drug on the degradable drug-loading stent to be improved, and the influence of the drug-loading groove 13 on the physical properties of the degradable drug-loading stent is controlled within the scope of the criteria for medical devices.

Specifically, referring to Tables 2 to 10, the degradable drug-loading stent shown in FIG. 3 was selected for physical performance testing, and the stents with diameters of 2.5 mm, 3.0 mm, and 4.0 mm were used for controlled experiments in groups. It should be noted that the diameter of the stent refers to the diameter of the mesh columnar structure in an expanded state. That is, the diameters of the selected mesh columnar structures corresponding to the several degradable drug-loading stent samples provided with the drug-loading groove 13 include 2.5 mm, 3.0 mm, and 4.0 mm. Also, a degradable stent with the same specifications and without drug-loading groove was used as a control sample for the physical performance testing for reference.

No. 1, 2, 3, and 4 in Tables 2 to 10 represent the stents No. 1, 2, 3, and 4 of the specification model. The wall thickness of the mesh columnar structure of stents No. 1 to 4 is about 125 μm, stents Nos. 1 and 2 are ungrooved stents, stents Nos. 3 and 4 are degradable drug-loading stents provided with drug-loading groove 13. The depth of the drug-loading groove 13 is controlled to be 40 μm to 60 μm, the groove width of the drug-loading groove 13 on the outer surface 10b is controlled to be 30±10 μm, and the groove line of the drug-loading groove 13 continuously wind around along the circumferential direction of the supporting unit ring 11.

The results of the radial anti-extrusion test are shown in the following tables:

TABLE 2

| 2.5 mm specification | No. | Radial anti-extrusion | Mean |
|---|---|---|---|
| Control sample | 1 | 93.24 Kpa | 94.53 Kpa |
| | 2 | 95.82 Kpa | |
| Grooved sample | 3 | 95.14 Kpa | 91.32 Kpa |
| | 4 | 87.49 Kpa | |

TABLE 3

| 3.0 mm specification | No. | Radial anti-extrusion | Mean |
|---|---|---|---|
| Control sample | 1 | 89.57 Kpa | 88.68 Kpa |
| | 2 | 87.59 Kpa | |
| Grooved sample | 3 | 86.31 Kpa | 84.635 Kpa |
| | 4 | 82.96 Kpa | |

TABLE 4

| 4.0 mm specification | No. | Radial anti-extrusion | Mean |
|---|---|---|---|
| Control sample | 1 | 87.02 Kpa | 87.29 Kpa |
| | 2 | 87.56 Kpa | |
| Grooved sample | 3 | 91.59 Kpa | 89.34 Kpa |
| | 4 | 87.09 Kpa | |

Tables 2 to 4 list the radial anti-extrusion data of the stents with diameters of 2.5 mm, 3.0 mm, and 4.0 mm, respectively. From Tables 2 to 4, it can be seen that the anti-extrusion performance of the samples 3 and 4 provided with the drug-loading groove 13 is equivalent to that of the control samples 1 and 2, that is to say, it still has a relatively good radial anti-extrusion performance after the drug-loading groove 13 is provided on the outer surface 10b of the mesh columnar structure.

The results of the stent over-expansion test are shown in the tables below:

TABLE 5

| 2.5 mm specification | No. | Fracture diameter |
|---|---|---|
| Control sample | 1 | 3.32 mm |
| | 2 | 3.35 mm |
| Grooved sample | 3 | 3.34 mm |
| | 4 | 3.39 mm |

TABLE 6

| 3.0 mm specification | No. | Fracture diameter |
|---|---|---|
| Control sample | 1 | 3.87 mm |
| | 2 | 3.87 mm |
| Grooved sample | 3 | 3.86 mm |
| | 4 | 3.8 mm |

TABLE 7

| 4.0 mm specification | No. | Fracture diameter |
|---|---|---|
| Control sample | 1 | 5.25 mm |
| | 2 | 5.19 mm |
| Grooved sample | 3 | 5.25 mm |
| | 4 | 5.31 mm |

In the stent over-expansion test, a fracture diameter is used as an index to measure the over-expansion performance. The fracture diameter refers to the diameter of the stent when the stent undergoes processing, storage, and aging under certain conditions, using a balloon to gradually expand the stent in water at 37° C. until the supporting unit ring 11 is fractured.

As shown in Tables 5 to 7, the fracture diameters of the samples 3 and 4 provided with the drug-loading groove 13 are equivalent to those of the control samples 1 and 2, that is to say, the over-expansion performance of the stents is slightly different and still relatively good after the drug-loading groove 13 is provided on the outer surface 10b of the mesh columnar structure.

The results of the axial retraction test are shown in the tables below:

TABLE 8

| 2.5 mm specification | No. | Axial retraction |
|---|---|---|
| Control sample | 1 | 2.05% |
| | 2 | 2.71% |
| Grooved sample | 3 | 2.13% |
| | 4 | 2.39% |

TABLE 9

| 3.0 mm specification | No. | Axial retraction |
|---|---|---|
| Control sample | 1 | 2.51% |
| | 2 | 3.15% |
| Grooved sample | 3 | 2.54% |
| | 4 | 2.05% |

TABLE 10

| 4.0 mm specification | No. | Axial retraction |
|---|---|---|
| Control sample | 1 | 2.66% |
| | 2 | 1.98% |
| Grooved sample | 3 | 2.12% |
| | 4 | 2.01% |

As shown in Table 8 to 10, as the stents of the same specification, the control samples 1, 2 and the samples 3, 4 provided with the drug-loading groove 13 have slightly different axial retraction within 5% for all, meeting the criteria for the use of stent medical devices.

The technical features of the embodiments described above may be arbitrarily combined. For the sake of brevity of description, not all possible combinations of the technical features in the aforementioned embodiments are described. However, as long as there is no contradiction between the combinations of these technical features, all should be considered as the scope of this specification.

The above embodiments only represent several examples of the present disclosure, and the description thereof is more specific and detailed, but it should not be construed as restricting the scope of the present disclosure. It should be understood that, the disclosures of the present disclosure are not limited to the above-described examples, and those skilled in the art can make modifications and changes in accordance with the above description, all of which are within the protection scope of the present disclosure. Therefore, the protection scope of the present disclosure shall be defined by the appended claims.

What is claimed is:

1. A degradable drug-loading stent, comprising a stent body, wherein the stent body is provided with a drug-loading groove at an outer surface thereof; the stent body has a contracted state and an expanded state, the stent body is capable of being switched from the contracted state to the expanded state by radial expansion, the stent body has a mesh columnar structure in the expanded state, and the drug-loading groove has a depth that is 10% to 60% of a wall thickness of the mesh columnar structure;

wherein the stent body comprises a plurality of supporting unit rings and connecting rods, the supporting unit rings are connected by the connecting rods to form the mesh columnar structure, and the drug-loading groove

--- is at least arranged on an outer surface of at least one of the supporting unit rings;

wherein the drug-loading groove on at least one of the supporting unit rings comprises a plurality of convoluted groove sections and a plurality of connecting groove sections, the convoluted groove sections and the connecting groove sections being arranged in series to form a substantially continuous groove path; and wherein each convoluted groove section has a denser groove line than a corresponding connecting groove section, such that the convoluted groove sections provide a greater localized drug-loading capacity relative to the connecting groove sections, thereby enabling site-specific drug administration.

2. The degradable drug-loading stent according to claim 1, wherein the stent body is made of biodegradable polymer.

3. The degradable drug-loading stent according to claim 1, wherein the depth of the drug-loading groove is 25% to 45% of the wall thickness of the mesh columnar structure.

4. The degradable drug-loading stent according to claim 1, wherein the depth of the drug-loading groove and a width of the drug-loading groove meet the following conditions:

$$Y = 120 - 2X;$$

where Y is the depth of the drug-loading groove, X is the width of the drug-loading groove, and Y is in a range of less than or equal to 80 microns.

5. The degradable drug-loading stent according to claim 1, wherein a cumulative groove length of the drug-loading groove on at least one of the supporting unit rings is 0.9 to 5 times a length of the supporting unit ring where the drug-loading groove is located.

6. The degradable drug-loading stent according to claim 1, wherein a groove width of the drug-loading groove on at least one of the supporting unit rings is 10% to 80% of a width of the supporting unit ring where the drug-loading groove is located.

7. The degradable drug-loading stent according to claim 1, wherein at least one of two supporting unit rings located at ends of the stent body is provided with a plurality of drug-loading grooves, the plurality of drug-loading grooves being arranged at intervals in a circumferential direction.

8. A method for manufacturing a degradable drug-loading stent, comprising:

processing and shaping a tube or stent parison using a biodegradable polymer;

processing the shaped tube or stent parison to form a stent body with a mesh columnar structure, the stent body being radially expandable and contractible;

providing a drug-loading groove on an outer surface of the mesh columnar structure, the drug-loading groove having a depth that is 10% to 60% of a wall thickness of the mesh columnar structure; wherein the drug-loading groove comprises a plurality of convoluted groove sections and a plurality of connecting groove sections, the convoluted groove sections and the connecting groove sections being arranged in series to form a substantially continuous groove path; and wherein each convoluted groove section has a denser groove line than a corresponding connecting groove section, such that the convoluted groove sections provide a greater localized drug-loading capacity relative to the connecting groove sections, thereby enabling site-specific drug administration.

9. The method for manufacturing the degradable drug-loading stent according to claim 8, wherein during providing the drug-loading groove, a focal point of a femtosecond laser moves on the outer surface of the mesh columnar structure at a moving speed S meeting the following condition:

$$V < S \leq 10V,$$

where V is a moving speed of the focal point of the femtosecond laser relative to the shaped tube or stent parison when the femtosecond laser processes the shaped tube or stent parison.

10. The method for manufacturing the degradable drug-loading stent according to claim 8, wherein a drug is filled into the drug-loading groove after providing the drug-loading groove.

11. The method for manufacturing the degradable drug-loading stent according to claim 10, wherein a surface of the stent body filled with the drug is polished.

\* \* \* \* \*